US00PP20667P2

(12) United States Plant Patent
Geibel

(10) Patent No.: US PP20,667 P2
(45) Date of Patent: Jan. 19, 2010

(54) ***ANGELONIA* PLANT NAMED 'ADEBIC'**
(50) Latin Name: *Angelonia hybrida*
Varietal Denomination: Adebic

(75) Inventor: Martin Geibel, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 392 days.

(21) Appl. No.: 11/820,016

(22) Filed: Jun. 15, 2007

(51) Int. Cl.
*A01H 5/00* (2006.01)

(52) U.S. Cl. ..... Plt./404
(58) Field of Classification Search ..... Plt./404
See application file for complete search history.

*Primary Examiner*—Kent L Bell
(74) *Attorney, Agent, or Firm*—C. A. Whealy

(57) ABSTRACT

A new and distinct cultivar of *Angelonia* plant named 'Adebic', characterized by its upright and compact plant habit; freely branching habit; freely flowering habit; large violet and white bi-colored flowers; and good garden performance.

1 Drawing Sheet

Botanical designation: *Angelonia hybrida.*
Cultivar denomination: 'Adebic'.

BACKGROUND OF THE INVENTION

The present invention relates to a new and distinct cultivar of *Angelonia*, botanically known as *Angelonia hybrida* and hereinafter referred to by the name 'Adebic'.

The new *Angelonia* is a product of a planned breeding program conducted by the Inventor in Dresden, Germany. The objective of the breeding program is to create new compact and freely-flowering *Angelonia* cultivars.

The new *Angelonia* originated from a cross-pollination made by the Inventor during the summer of 2003 in Dresden, Germany of two unnamed proprietary selections of *Angelonia hybrida*, not patented. The new *Angelonia* was discovered and selected by the Inventor as a single flowering plant within the progeny of the stated cross-pollination in a controlled environment in Dresden, Germany during the summer of 2004.

Asexual reproduction of the new *Angelonia* by cuttings in a controlled environment in Dresden, Germany since December, 2004, has shown that the unique features of this new *Angelonia* are stable and reproduced true to type in successive generations.

SUMMARY OF THE INVENTION

The cultivar Adebic has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Adebic'. These characteristics in combination distinguish 'Adebic' as a new and distinct cultivar of *Angelonia:*

1. Upright and compact plant habit.
2. Freely branching habit.
3. Freely flowering habit.
4. Large violet and white bi-colored flowers.
5. Good garden performance.

Plants of the new *Angelonia* differ from plants of the parent selections primarily in flower color and plant size.

Plants of the new *Angelonia* can be compared to plants of the cultivar Anwedg, disclosed in U.S. Plant patent application Ser. No. 11/731,872. Plants of the new *Angelonia* and the cultivar Anwedg differ in the following characteristics:

1. Plants of the new *Angelonia* are more compact than plants of the cultivar Anwedg.
2. Plants of the new *Angelonia* have shorter internodes than plants of the cultivar Anwedg.
3. Plants of the new *Angelonia* are more freely flowering and have denser inflorescences than plants of the cultivar Anwedg.

BRIEF DESCRIPTION OF THE PHOTOGRAPH

The accompanying colored photograph illustrates the overall appearance of the new *Angelonia*, showing the colors as true as it is reasonably possible to obtain in colored reproductions of this type. Colors in the photograph may differ slightly from the color values cited in the detailed botanical description which accurately describe the colors of the new *Angelonia*. The photograph comprises a side perspective view of a typical flowering plant of 'Adebic' grown in a container.

DETAILED BOTANICAL DESCRIPTION

The aforementioned photograph and followi ng observations, measurements and values describe plants grown in Dresden, Germany in containers and under commercial practice in a glass-covered greenhouse with day temperatures averaging 20° C., night temperatures averaging 16° C. and light levels ranging from 15 kilolux to 100 kilolux. Plants were pinched twice, two and five weeks after planting. Plants had been growing for about five months when the photograph and description were taken. In the following description, color references are made to The Royal Horticultural Society Colour Chart, 1995 Edition, except where general terms of ordinary dictionary significance are used.

Botanical classification: *Angelonia hybrida* cultivar Adebic.

Parentage:

*Female, or seed, parent.*—Unnamed proprietary selection of *Angelonia hybrida*, not patented.

*Male, or pollen, parent.*—Unnamed proprietary selection of *Angelonia hybrida*, not patented.

Propagation:

*Type.*—By cuttings.

*Time to initiate roots.*—About 20 days at 20° C.

*Time to produce a rooted young plant.*—About four weeks at 20° C.

*Root description.*—Fine, fibrous; white in color.

*Rooting habit.*—Freely branching; moderately dense.

Plant description:

*Plant form/habit.*—Herbaceous perennial. Upright and compact plant habit; broad inverted triangle. Freely branching habit; when pinched, lateral branches form at the nodes. Vigorous growth habit.

*Plant height.*—About 45 cm.

*Plant width (spread).*—About 35 cm.

*Lateral branches.*—Length: About 30 cm. Diameter: About 3 mm. Internode length: About 2.5 cm. Strength: Moderately strong to strong. Texture: Slightly pubescent. Color: 144B.

Foliage description:

*Arrangement.*—Opposite, decussate; simple; sessile.

*Length.*—About 4 cm to 9 cm.

*Width.*—About 1.5 cm to 2 cm.

*Shape.*—Lanceolate to oblong.

*Apex.*—Acute.

*Base.*—Attenuate.

*Margin.*—Serrate.

*Texture, upper and lower surfaces.*—Smooth, glabrous.

*Venation pattern.*—Pinnate.

*Color.*—Developing and fully expanded leaves, upper surface: 137A; venation, 137A. Developing and fully expanded leaves, lower surface: 137B; midvein, 145C; lateral veins, close to 137B.

Flower description:

*Flower type/habit.*—Single flowers arranged in terminal racemes; flowers face mostly outward. Freely flowering habit; dense inflorescences.

*Fragrance.*—None detected.

*Natural flowering season.*—Continuously flowering from mid-May until frost in Central Europe. Flowers not persistent.

*Postproduction longevity.*—Flowers last about 20 days on the plant.

*Flower buds.*—Height: About 5 mm. Diameter: About 5 mm. Shape: Globular. Color: 138A.

*Inflorescence height.*—About 20 cm.

*Inflorescence diameter.*—About 8 cm.

*Flower diameter.*—About 3 cm by 3 cm.

*Flower depth.*—About 1 cm.

*Petals.*—Quantity per flower: Typically five in a single whorl; petals fused at the base. Length: About 1 cm. Width: About 1.5 cm. Shape: Roughly spatulate. Apex: Rounded. Margin: Entire; undulate. Texture, upper and lower surface s: Smooth, glabrous; velvety. Color: When opening and fully opened, upper surface: Upper two petals, 87A; lateral petals, 87A, becoming closer to 155D with development; lower petal, close to 155D; throat, close to 4A. When opening and fully opened, lower surface: Upper two petals, 87B; lateral petals, 87B, becoming closer to 155D with development; lower petal, close to 155D.

*Sepals.*—Quantity per flower: Typically five in a single whorl. Length: About 5 mm. Width: About 3 mm. Shape: Lanceolate. Apex: Acute. Margin: Entire. Texture, upper and lower surfaces: Smooth, glabrous. Color, upper and lower surfaces: 139B.

*Pedicels.*—Length: About 2 cm to 3 cm. Diameter: About 1 mm. Angle: About 90° from vertical. Strength: Moderately strong; flexible. Texture: Smooth, glabrous. Color: 146A.

*Reproductive organs.*—Stamens: Quantity per flower: Typically four. Filament length: About 3 mm. Filament color: Close to 155D. Anther shape: Elliptic. Anther length: About 2 mm. Anther color: Brown to grey. Pollen amount: Moderate. Pollen color: Close to 155D. Pistils: Quantity per flower: One. Pistil length: About 5 mm. Stigma shape: Tapering. Stigma color: Close to 155D. Style length: About 4 mm. Style color: Close to 155D. Ovary color: Close to 144A.

*Fruits.*—Length: About 5 mm. Diameter: About 5 mm. Color: 177B.

*Seeds.*—Quantity per flower: About 30 to 50. Length: Less than 1 mm. Diameter: Less than 1 mm. Color: Light brown.

Disease/pest resistance: Plants of the new *Angelonia* have not been noted to be resistant to pathogens and pests common to *Angelonia.*

Garden performance: Plants of the new *Angelonia* have been observed to have good garden performance and tolerate rain, wind and temperatures ranging from about 1° C. to 35° C.

It is claimed:

1. A new and distinct *Angelonia* plant named 'Adebic' as illustrated and described.

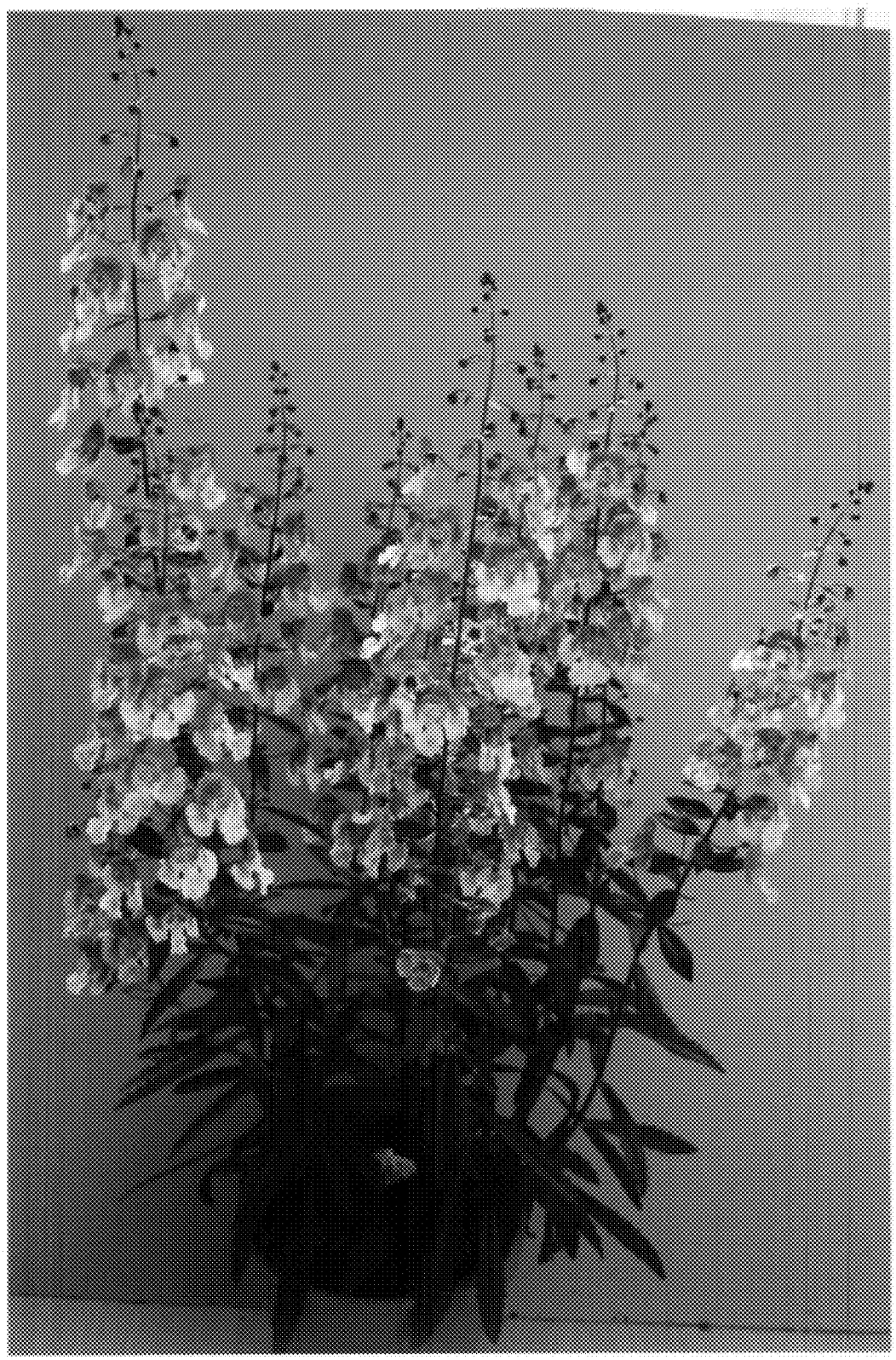

* * * * *